United States Patent
Lin et al.

(10) Patent No.: US 7,015,424 B2
(45) Date of Patent: Mar. 21, 2006

(54) HEAT GENERATOR

(75) Inventors: Jhy-Chain Lin, Tu-Cheng (TW); Ga-Lane Chen, Fremont, CA (US)

(73) Assignee: Hon Hai Precision Industry Co., Ltd., (TW)

( * ) Notice: Subject to any disclaimer, the term of this patent is extended or adjusted under 35 U.S.C. 154(b) by 0 days.

(21) Appl. No.: 10/951,360

(22) Filed: Sep. 28, 2004

(65) Prior Publication Data

US 2005/0139586 A1 Jun. 30, 2005

(30) Foreign Application Priority Data

Dec. 26, 2003 (TW) ............................... 92222764 U

(51) Int. Cl.
*H05B 1/02* (2006.01)
*H05B 3/28* (2006.01)
*G01N 25/18* (2006.01)
*F25B 21/02* (2006.01)

(52) U.S. Cl. ...................... 219/385; 219/201; 219/494; 374/44

(58) Field of Classification Search ................ 219/385, 219/386, 200, 201, 228, 494, 497; 62/3.2, 62/3.3, 3.7; 374/44
See application file for complete search history.

(56) References Cited

U.S. PATENT DOCUMENTS

| | | | |
|---|---|---|---|
| 3,114,255 A | * | 12/1963 | Niven ........................... 374/44 |
| 3,662,587 A | * | 5/1972 | Allen et al. ..................... 374/44 |
| 3,733,887 A | * | 5/1973 | Stanley et al. ................. 374/44 |
| 4,929,089 A | | 5/1990 | Tsuchida ....................... 374/44 |
| 5,258,929 A | * | 11/1993 | Tsuchida ...................... 702/136 |
| 6,550,961 B1 | | 4/2003 | Ueda ............................ 374/44 |
| 2003/0072349 A1 | | 4/2003 | Osone et al. .................. 374/43 |

FOREIGN PATENT DOCUMENTS

DE 2724846 A * 12/1978

* cited by examiner

*Primary Examiner*—Joseph Pelham
(74) *Attorney, Agent, or Firm*—Morris, Manning & Martin, LLP; Tim Tingkang Xia, Esq.

(57) ABSTRACT

A heat generator includes a heat generating member including a heat flow output face, a heat flow insulative member attachably surrounding the heat generating member except the heat flow output face for insulating the heat generating member except the heat flow output face, a heat flow compensating member attachably surrounding the heat flow insulative member but exposing the heat flow output face to allow it contacting with a specimen, and a heat flow compensating circuit connected between the heat flow insulative member and the heat flow compensating member. The circuit is capable of controlling heat generated by the heat flow compensating member to cause no heat flow flowing between the heat flow compensating member and the heat flow insulative member whereby the heat energy of the heat flow outputing from the heat flow output face of the heat generating member is equal to the heat energy of heat generated by the heat generating member.

14 Claims, 1 Drawing Sheet

US 7,015,424 B2

HEAT GENERATOR

CROSS-REFERENCE TO RELATED APPLICATIONS

This application is related to U.S. application Ser. No. 10/930,551, filed on Aug. 31, 2004, and U.S. application Ser. No 10/977,723, filed on Oct. 29, 2004. The disclosures of the above identified applications are incorporated herein by reference.

TECHNICAL FIELD

The present invention relates to a heat generator, and particularly to a heat generator having heat flow compensation capability.

BACKGROUND

When developing new material, especially heat conduct material, it need to measure the heat conductivity of the material. When designing a heat dissipation device for electronic devices, the designer need to know the heat conduct capability of the material of the heat dissipation device. Precisely measuring heat conductivity of the material is the key of the design.

In early times, the heat conductivity of a material is measured via sandwiching a specimen made of the material between a heat source and an object with a lower temperature. The heat generated by the heat source flows through the specimen to the object with lower temperature. A temperature gradient $\Delta T$ exists between two opposite ends of the specimen. The distance between the two opposite ends of the specimen $\Delta X$ can be measured. Assuming that all of the heat generated by the heat source flow through the specimen, the heat energy Q of the heat flow flowing through the specimen is equal to the heat energy Q' generated by the heat source. The heat energy Q' generated by the heat source is calculated according to the equation as follows:

$$Q' = \alpha I^2 R$$

wherein R is the resistance value of a thermal resistor embedded in the heat source, I represents the electric current flowing through the thermal resistor, and $\alpha$ is a ratio of electrical power converted to heat energy of the thermal resistor. The heat conductivity K of the material of the specimen can be calculated according to the equation as follows:

$$K = q \ast \Delta X / \Delta T$$

q represents heat flow which is the rate at which heat energy Q flows through the specimen per square meter, in $W/m^2$.

In the above method, the specimen firmly contact with one face of the heat source. The other faces of the heat source are heat insulated by a layer of insulative material covered thereon in order to ensure all of the heat generated by the heat source flow through the specimen. However, the insulative capability of the insulative material, such as alumina, is limited. Some of the heat generated by the heat source is inevitably dissipated through the other faces which do not contact the specimen. That means, the heat energy Q flowing through the specimen is not equal to the heat energy Q' generated by the heat source. Thus, the value of the heat flow q flowing through the specimen exists an inaccuracy which results in the calculated value of the heat conductivity K of the material of the specimen existing an inaccuracy.

SUMMARY OF THE INVENTION

Accordingly, an object of the present invention is to provide a heat generator which can output a predetermined heat flow precisely.

To achieve the above-mentioned object, a heat generator in accordance with the present comprises a heat generating member comprising a heat flow output face, a heat flow insulative member attachably surrounding the heat generating member except the heat flow output face for insulating the heat generating member except the heat flow output face, a heat flow compensating member attachably surrounding the heat flow insulative member but exposing the heat flow output face to allow it to contact with a specimen, and a heat flow compensating circuit electrically connected between the heat flow insulative member and the heat flow compensating member. The circuit is capable of controlling heat generated by the heat flow compensating member to cause no heat flow flowing between the heat flow compensating member and the heat flow insulative members, whereby the heat energy of the heat flow outputting from the heat flow output face of the heat generating member is equal to the heat energy of heat generated by the heat generating member.

Other objects, advantages and novel features of the present invention will be drawn from the following detailed description of a preferred embodiment of the present invention with attached drawings, in which:

DESCRIPTION OF A PREFERRED EMBODIMENT

Figure 1:
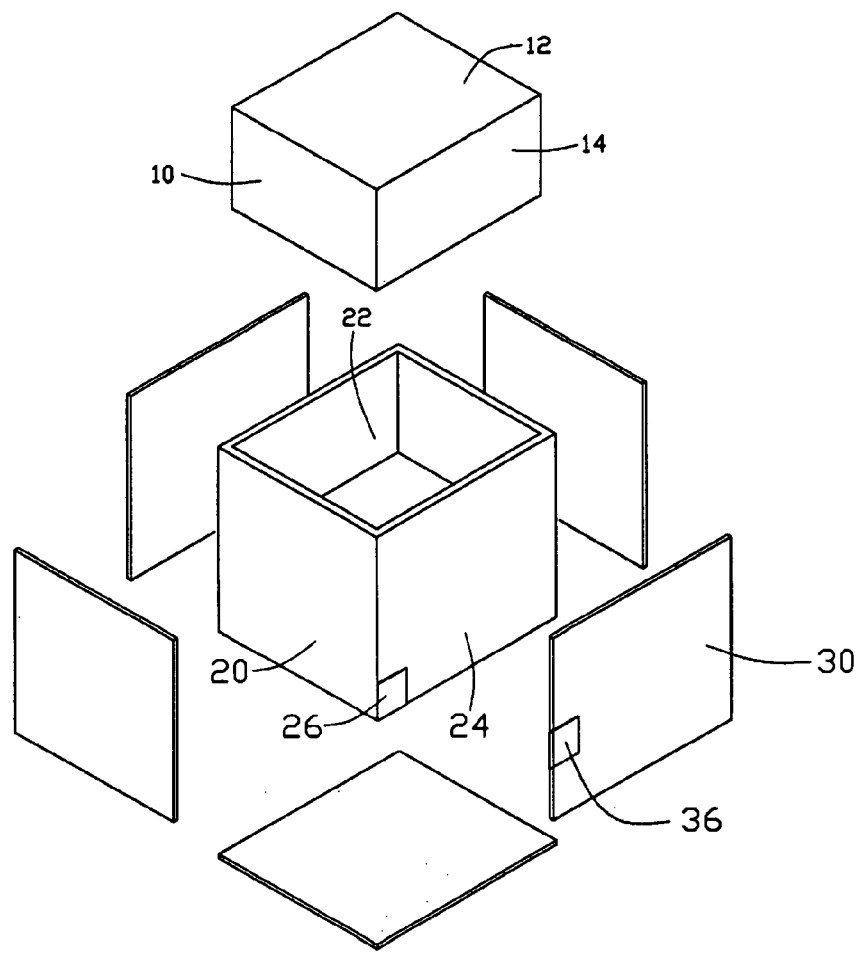
FIG. 1 is an exploded view of a heat generator in accordance with an embodiment of the present invention.

Referring to FIG. 1, a heat generator in accordance with the preferred embodiment of the present invention comprises a heat generating member 10, a heat flow insulative member 20 and a heat flow compensating member.

The heat generating member 10 is a polyhedron. In the preferred embodiment, we take a cube shape employed as an example of the heat generating member 10. The heat generating member 10 comprises six faces. One face 12 is used as a heat flow output face and the other five faces 14 are used as heat flow insulative faces that no heat flow flows therethrough. A thermal resistor (not visible) is embedded in the heat generating member 10 for generating a predetermined heat energy. The quantity Q' of the heat energy generated by the thermal resistor is calculated according to the following equation $$Q' = \alpha I^2 R.$$

wherein R is the resistance value of the thermal resistor, I represents the electric current flowing through the thermal resistor, and a is a ratio of electrical power converted to heat energy.

The heat flow insulative member 20 is made of heat insulative material. The heat flow insulative member 20 is cube shaped and comprises five heat insulative walls 24 with a cavity 22 formed therebetween. The depth of the cavity 22 is equal to the height of the heat generator member 10. The heat generating member 10 is accommodated in the cavity 22 of the heat flow insulative member 20 and the five heat insulative walls 24 of the heat flow insulative member 20 cover the corresponding heat insulative faces 14 of the heat generating member 10 for insulating the heat insulative faces 14. The heat flow output face 12 of the heat generating member 10 is exposed for contacting with a specimen (not shown). A thermistor 26 is installed on each heat insulative wall 24 of the heat flow insulative member 20 for sensing the temperature of the heat insulative wall 24.

The heat flow compensating member comprises five heat flow compensating plates 30 which are attached on the five heat insulative walls 24 of the heat flow insulative member 20 respectively to cause the heat flow compensating member surround the heat flow insulative member 20 but exposing the heat flow output face 12 of the heat generating member 10. Each heat flow compensating plate 30 comprises a heat flow compensating face contacting the corresponding heat insulative wall 24. A thermal resistor (not visible) is embedded in each of the heat flow compensating plates 30 for generating heat. The temperature of the heat flow compensating face is adjustable when the electric current flowing through the thermal resistor is adjusted. A thermistor 36 is installed on the heat flow compensating face of each heat flow compensating plate 30 for sensing the temperature of the heat flow compensating face.

Figure 2:
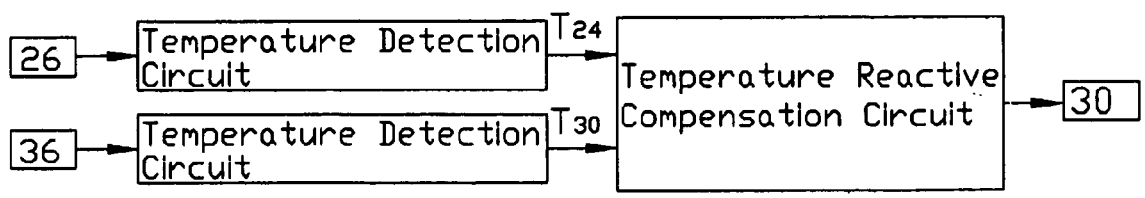
FIG. 2 is a diagram showing the heat flow compensating circuit of the heat generator.

FIG. 2 shows a heat flow compensating circuit electrically connected between the thermistors 26, 36. The hear flow compensating circuit comprises two temperature detection circuits electrically connected to the thermistors 26,36 respectively, and a temperature reactive compensating circuit electrically connected to the hear flow compensating plate 30. The two temperature detection circuits are used to sense the temperature of the beat flow insulative wall 24 and the heat flew compensating face of the heat flow compensating plate 30 and output a pair of corresponding temperature signals T24, T30 to the temperature reactive compensating circuit simultaneously. When the temperature of the heat flow compensating face of the heat flow compensating plate 30 is not equal to that of the heat flow insulative wall 24, the temperature reactive compensating circuit outputs an adjusted electric current to the thermal resistor of the heat flow compensating plate 30 to adjust the temperature of the heat flow compensating face of the hear flow compensating plate 30 to thereby cause the temperature of the heat flow compensating face of the heat flow compensating plate 30 to be equal to the temperature of the heat flow insulative wall 24 of the heat flow insulative member 20. Thus, no heat flow flows between the heat flow insulative wall 24 of the heat flow insulative member 20 and the hear flow compensating place 30, thereby preventing small amounts of heat transferred from the heat flow insulative face 14 of the heat generating member 10 to the heat insulative wall 24 of the heat flow insulative member 20 from being dissipated. Accordingly, almost all of the hear generated by the heat generating member 10 is transferred from the heat flow output face 12 of the heat generating member 10 to the specimen. Therefore, the heat energy Q flowing through the specimen is substantially equal to the heat energy Q' generated by the heat generating member 10 and a predetermined heat flow is able to be precisely transferred from the heat generator.

Alternatively, the heat flow compensating plates 30 are thermoelectric coolers which work based on the peltier effect. That is, when the thermoelectric cooler 30 is electrified it forms one heating face with a uniform temperature and one cooling face opposite to the heating face. The heating face of the thermoelectric cooler 30 contacts with the corresponding heat insulative wall 24 acting as a heat flow compensating face. The temperature of the heating face of thermoelectric cooler 30 is adjustable when the electric current flowing through the thermoelectric cooler 30 is adjusted. The temperature of the heating face of thermoelectric cooler 30 is adjustable when the electric current flowing through the thermoelectric cooler 30 is adjusted.

In the present invention, the heat flow insulative member 20 surrounds the heat generating member 10 except the heat flow output face 12. Accordingly, large amounts of heat generated by the heat generating member 10 is insulated by the heat flow insulative member 20 and only small amounts of heat is transferred to the heat flow insulative member 20. The small amounts of heat is transferred to and compensated by the heat flow compensating member 30 to thereby maintain a state of no heat flow flowing between the heat flow compensating member 30 and the heat flow insulative member 20. Thus, the heat flow compensating member 30 of the present invention consumes smaller amounts of electrical energy compared with a heat flow compensating member of a heat generator in which the heat flow compensating member directly contacts with heat flow insulative faces of a heat generating member.

It is understood that the invention may be embodied in other forms without departing from the spirit thereof. Thus, the present example and embodiment is to be considered in all respects as illustrative and not restrictive, and the invention is not to be limited to the details given herein.

What is claimed is:

1. A heat generator comprising:
   a heat generating member for generating heat, comprising a heat flow output face and a plurality of heat flow insulative faces;
   a heat flow insulative member having a plurality of heat flow insulative walls covering the heat flow insulative faces respectively for insulating the heat flow insulative faces;
   a heat flow compensating member having a plurality of heat flow compensating faces covering the heat flow insulative walls respectively; and
   a heat flow compensating circuit electrically connected between the heat flow insulative member and the heat flow compensating member for maintaining a state of no heat flow flowing between the heat flow compensating member and the corresponding heat flow insulative wall, whereby the heat energy of the heat flow outputting from the heat flow output face is equal to the heat energy of the heat generated by the heat generating member.

2. The heat generator as claimed in claim 1, wherein a first thermistor is provided at each of the heat flow insulative faces, and a second thermistor is provided at each of the heat flow compensating faces of the heat flow compensating member.

3. The heat generator as claimed in claim 2, wherein the heat flow compensating circuit comprises two temperature detection circuits connected to the first and second thermistors respectively for sensing the temperature of each heat flow insulative face and the heat flow compensating face of heat flow compensating member, and a temperature reactive compensating circuit connected to the heat flow compensating member for outputting an adjusted current to the heat flow compensating member when the temperature of any of the heat flow insulative faces and the corresponding heat flow compensating face of the heat flow compensating member are not equal to each other, to adjust the temperature of the heat flow compensating face of the heat flow compensating member to thereby cause the temperature of the heat flow compensating face of the heat flow compensating member to be equal to the temperature of the heat flow insulative face.

4. The heat generator as claimed in claim 3, wherein the heat generating member is a polyhedron.

5. The heat generator as claimed in claim 4, wherein the heat generating member is a cube with five heat insulative faces.

6. The heat generator as claimed in claim 5, wherein the heat flow insulative member defines a cavity for accommodating the heat generating member therein.

7. The heat generator as claimed in claim 3, wherein the heat flow compensating member comprises a plurality of heat flow compensating plates in each of which a thermal resistor is installed.

8. The heat generator as claimed in claim 3, wherein the heat flow compensating member comprises a plurality of theremoelectric coolers, each of which, when electrified, forms one heating face with a uniform temperature acting as one of the heat flow compensating faces and one cooling face opposite to the heating fade.

9. A heat generator comprising:
a heat generating member comprising heat flow output face;
a heat flow insulative member attachably surrounding the heat generating member except the heat flow output face for insulating large amounts of heat generated by the heat generating member;
a heat flow compensating member surrounding the heat flow insulative member but exposing the heat flow output face of the heat generating member for compensating heat transferred to the heat flow insulative member from the heat generating member; and
a heat flow compensating circuit electrically connecting between the heat flow insulating member and the heat flow compensating member for maintaining a state of no heat flowing between the heat flow compensating member and the heat flow insulative member by controlling performance of the heat flow compensating member.

10. The heat generator as claimed in claim 9, wherein the heat flow compensating member comprises a heat flow compensating face contacting with the heat flow insulative member.

11. The heat generator as claimed in claim 10, wherein the heat flow compensating circuit comprises two temperature detection circuits electrically connected to the beat flow insulative member and the heat flow compensating face of the heat flow compensating member respectively for sensing the temperatures thereof, and a temperature reactive compensating circuit electrically connected to the heat flow compensating member for outputting an adjusted current to the heat flow compensating member when the temperature of the heat flow insulative member and the heat flow compensating face are not equal to each other, to adjust the temperature of the heat flow compensating face to thereby cause the temperature of the heat flow compensating face to be equal to the temperature of the heat flow insulative member.

12. A method for a heat generator to provide constant heat, comprising steps of:
operating said heat generator to create said heat and offer said heat from a side thereof;
placing a heat flow insulative member attachably around said heat generator other than said side of said heat generator;
placing a heat flow compensating member around said heat flow insulative member; and
operating said heat flow compensating member to provide heat to said heat generator via said heat flow insulative member.

13. The method as claimed in claim 12, wherein said heat flow compensating member comprises at least one thermal resistor therein to provide said heat to said heat generator.

14. The method as claimed in claim 12, wherein said heat flow compensating member comprises at least one thermoelectric cooler therein to provide said heat to said heat generator.

* * * * *